US008694073B2

(12) United States Patent
Renshaw

(10) Patent No.: US 8,694,073 B2
(45) Date of Patent: Apr. 8, 2014

(54) PREDICTING EFFICACY OF PSYCHIATRIC TREATMENT

(75) Inventor: Perry Renshaw, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 1210 days.

(21) Appl. No.: 12/580,226

(22) Filed: Oct. 15, 2009

(65) Prior Publication Data

US 2010/0094120 A1  Apr. 15, 2010

Related U.S. Application Data

(60) Provisional application No. 61/105,777, filed on Oct. 15, 2008.

(51) Int. Cl.
A61B 5/05 (2006.01)
(52) U.S. Cl.
USPC ........... 600/414; 600/410; 600/411; 600/301; 424/9.1; 424/9.37
(58) Field of Classification Search
USPC ........... 600/410, 411, 414, 301; 424/9.1, 9.37
See application file for complete search history.

(56) References Cited

U.S. PATENT DOCUMENTS

2008/0287774 A1* 11/2008 Katz-Brull .................. 600/414
2010/0010336 A1*  1/2010 Pettegrew et al. ........... 600/410
2010/0280332 A1* 11/2010 Hyde et al. .................. 600/301

OTHER PUBLICATIONS

Dan V. Iosifescu, et al., Brain Bioenergetics and Response to Triiodothyronine Augmentation in Major Depressive Disorder, Biol Psychiatry 2008; 63: pp. 1127-1134.
Sarah Rubenstein, Elevated Rate of Teen Suicide Stirs Concern, Wall Street Journal, Sep. 3, 2008.
Brent P. Forester, et al., Phosphorus Magnetic Resonance Spectroscopy Study of Tissue Specific Changes in High Energy Phosphates Before and After Sertaline Treatment of Geriatric Depression, International Journal of Geriatric Psychiatry 2009; 24: pp. 788-797.
Constance M. Moore, et al., Lower Levels of Nucleoside Triphosphate in the Basal Ganglia of Depressed Subjects: A Phosporous-31 Magnetic Resonance Spectroscopy Study, Am J Psychiatry 1997; 154: pp. 116-118.
Hans-Peter Volz, et al., $^{31}$P Magnetic Resonance Spectroscopy in the Frontal Lobe of Major Depressed Patients, Eur Arch. Psychiatry Clin. Neuroscience 1998; 248: pp. 289-295.

* cited by examiner

Primary Examiner — Joel Lamprecht
(74) Attorney, Agent, or Firm — James W. Hill; McDermott Will & Emery LLP

(57) ABSTRACT

Methods and systems are described for determining, in a patient that suffers from a mood disorder (e.g., depression), a propensity of the patient to manifest reduced symptoms or levels of indicators of the mood disorder in response to a psychiatric treatment. This can involve determining levels of a marker (e.g., a metabolite) indicative of a brain bioenergetic state of the patient that is predictive of whether the patient will response favorably to an antidepression treatment. Such bioenergetic state markers, tending to normalize in response to antidepression therapy, can include, e.g., a pH, a magnesium level, and a phosphorus level. Brain levels of such markers can be determined by, e.g., $^{31}$P MRS.

20 Claims, 3 Drawing Sheets

PREDICTING EFFICACY OF PSYCHIATRIC TREATMENT

RELATED APPLICATIONS

This application claims priority benefit of U.S. Provisional Application No. 61/105,777, filed Oct. 15, 2008, the entirety of which is incorporated herein by reference.

FIELD

Some embodiments of the inventions described herein relate to treatment of psychiatric disorders, such as depression. More particularly, some embodiments relate to predicting efficacy of various psychiatric treatments, such as antidepressant drugs.

BACKGROUND

Positron emission tomography (PET) studies have shown abnormalities in glucose use rates and blood flow in certain brain regions, such as the anterior cingulate and the amygdala/hippocampus complex, of subjects with mood disorders, such as depression, seem to normalize in response to antidepressant treatment. For instance, magnetic resonance spectroscopy (1H MRS) studies have shown abnormalities of energy-intensive cellular membrane phospholipid metabolism, as measured by altered choline/creatine ratios, in the orbitofrontal cortex of depressed subjects. Observations of altered brain 1H MRS choline levels in depressed patients appear to be consistent with altered brain energy metabolism.

A limited number of studies have addressed changes in brain energy metabolism as measured by phosphorus ($^{31}$P) MRS in MDD subjects. This literature describes certain abnormalities in bioenergetic metabolism, primarily a decreased baseline level of β-nucleoside triphosphate (β-NTP) and total NTP in the basal ganglia and the frontal lobes of MDD subjects as compared to normal control subjects. Previous studies do not reliably indicate whether brain bioenergetic abnormalities in MDD represent a biological trait of subjects at risk for MDD or whether subjects at risk for MDD are dependent on the state and severity of depression.

Thyroid hormones, especially triiodothyronine (T3), have been shown effective as an augmentation strategy in treatment resistant depression (TRD). Data from previously published reports support their role for augmentation of tricyclic antidepressant drugs, and some studies have indicated a moderate efficacy of thyroid hormones as adjuvants to selective serotonin reuptake inhibitors (SSRI) in TRD.

SUMMARY OF THE INVENTION

Some embodiments of the inventions disclosed include methods for determining, in a patient that suffers from depression, a propensity of the patient to manifest reduced symptoms of depression in response to an antidepression treatment. Some embodiments comprise determining, in a brain of a patient that suffers from depression, levels of a marker (e.g., a metabolite) indicative of a brain bioenergetic metabolic state of the patient, the brain bioenergetic metabolic state being predictive as to whether the patient will manifest reduced symptoms of depression in response to a depression treatment. Certain embodiments of the present invention provide a method for determining, in a patient that has depression, a propensity of the patient to manifest a reduced level of depression in response to an antidepression treatment modality comprising: determining, in a patient that has depression, a first level of a metabolic marker in the patient's brain; comparing the first level of the marker to a second level of the marker, the second level comprising at least one of a value and a range of values of the marker in the brain of at least one subject that, while having depression, was not substantially responsive to the treatment modality; determining, based on a difference between the first level and the second level, a likelihood that the patient would be substantially responsive to the treatment modality if the treatment modality were administered to the patient; outputting an indicator of the likelihood to an output device. The likelihood may be based on statistical parameters such as hazard ratios or odds ratios derived from prior clinical studies.

In some embodiments, the marker comprises at least one of total adenosine triphosphate, adenosine diphosphate, and phosphocreatine. In certain embodiments, the marker comprises at least one of magnesium, pH, total nucleoside triphosphate, and β NTP. In certain embodiments, the marker comprises phosphocreatine, and wherein the treatment modality is effective to reduce the level of phosphocreatine in the patient. In some embodiments, the first and second levels of the marker are determined by $^{31}$P magnetic resonance spectroscopy. In certain embodiments, the marker is detected in a region of the brain comprising at least one of the anterior cingulate, the amygdala, and the hippocampus of the brain.

In some embodiments, the depression comprises a mood disorder, such as depression or bipolar disorder. major depressive disorder. In certain embodiments, the treatment modality comprises administering a thyroid hormone to the patient. In certain embodiments, the output device comprises at least one of a machine readable medium, a display screen, an LCD, a computer memory, and a paper or other writing object.

In some embodiments, the patient is under 20 years of age. In some embodiments, the patient is 60 years of age or older.

In some embodiments, the treatment modality comprises administering a serotonin reuptake inhibitor.

Some embodiments include a method for determining, in a patient that has a mood disorder, an expectation of the patient to manifest a reduced severity of the mood disorder in response to a treatment modality, the method comprising: determining, in a patient that has a mood disorder, a first level of a metabolic marker in the patient's brain; comparing the first level to a second level of the marker, the second level comprising at least one of a value and a range of values of the marker in the brain of at least one subject that, while having the mood disorder, was exposed to the treatment modality; determining, based on a difference between the first level and the second level, a likelihood the patient would be significantly responsive to the treatment modality; and outputting an indicator of the likelihood to an output device.

In some embodiments, the mood disorder comprises at least one of a depression and bipolar disorder. In some embodiments, the mood disorder comprises at least one of major depression, dysthymia, and depressive disorder not otherwise specified.

In some embodiments, the marker comprises at least one of adenosine triphosphate, adenosine diphosphate, and phosphocreatine. In some embodiments, the first and second levels of the marker are determined by $^{31}$P magnetic resonance spectroscopy or MR spectroscopy of another suitable isotope.

The marker can comprise at least one of magnesium, pH, total nucleoside triphosphate, and β NTP. The marker can also be any other known to those of skill in the art. In some embodiments, the marker comprises phosphocreatine, and wherein the treatment modality is effective to reduce a level of phosphocreatine in a human subject.

The treatment modality can comprise administering a thyroid hormone to the patient.

The output device can comprise at least one of a computer readable medium, a computer memory, a display screen, an LCD, and a paper.

In some embodiments, the marker is detected in a region comprising at least one of the anterior cingulate, the amygdala, and the hippocampus of the brain.

In some embodiments, the treatment modality comprises administering at least one of a serotonin reuptake inhibitor, a tricyclic antidepressant, an antipsychotic medication, and electroconvulsive therapy.

Some embodiments include a computer-implemented system for determining, in a patient that has a mood disorder, an expectation of the patient to manifest a reduced severity of the mood disorder in response to a treatment, the system comprising: an input module, configured to receive an indicator of a first level of a metabolic marker in the patient's brain; a processing module, configured for: (a) comparing the first level to a second level of the marker, the second level comprising at least one of a value and a range of values of the marker in the brain of at least one subject that, while having the mood disorder, was exposed to the treatment; and (b) determining, based on a difference between the first level and the second level, a likelihood the patient would be significantly responsive to the treatment; and an output module, configured to output an indicator of the likelihood to an output device.

In some embodiments of the system, the output device comprises at least one of a computer readable medium, a computer memory, a display screen, an LCD, and a paper. In some embodiments, the system further includes the output device.

In some embodiments, the mood disorder comprises at least one of a depression and bipolar disorder. In some embodiments, the mood disorder comprises at least one of major depression, dysthymia, and depressive disorder not otherwise specified.

Some embodiments of the system comprise at least one of computer software and computer hardware. In some embodiments of the system, the processing module comprises computer-executable instructions for the comparing and the determining.

In some embodiments of the system, the marker comprises at least one of adenosine triphosphate, adenosine diphosphate, and phosphocreatine. In some embodiments, the first and second levels of the marker are determined by $^{31}$P magnetic resonance spectroscopy or other appropriate isotope known to the skilled artisan. In some embodiments of the system, the marker comprises at least one of magnesium, pH, total nucleoside triphosphate, and β NTP.

In some embodiments of the system, the marker comprises phosphocreatine, and wherein the treatment modality is effective to reduce a level of phosphocreatine in a human subject.

In some embodiments of the system, the treatment modality comprises administering a thyroid hormone to the patient. In some embodiments of the system, the patient is under 20 years of age, or is 60 years of age or older.

In some embodiments of the system, the marker is detected in a region comprising at least one of the anterior cingulate, the amygdala, and the hippocampus of the brain.

In some embodiments of the system, the treatment modality comprises administering at least one of a serotonin reuptake inhibitor, a tricyclic antidepressant, an antipsychotic medication, and electroconvulsive therapy.

Figure 2:
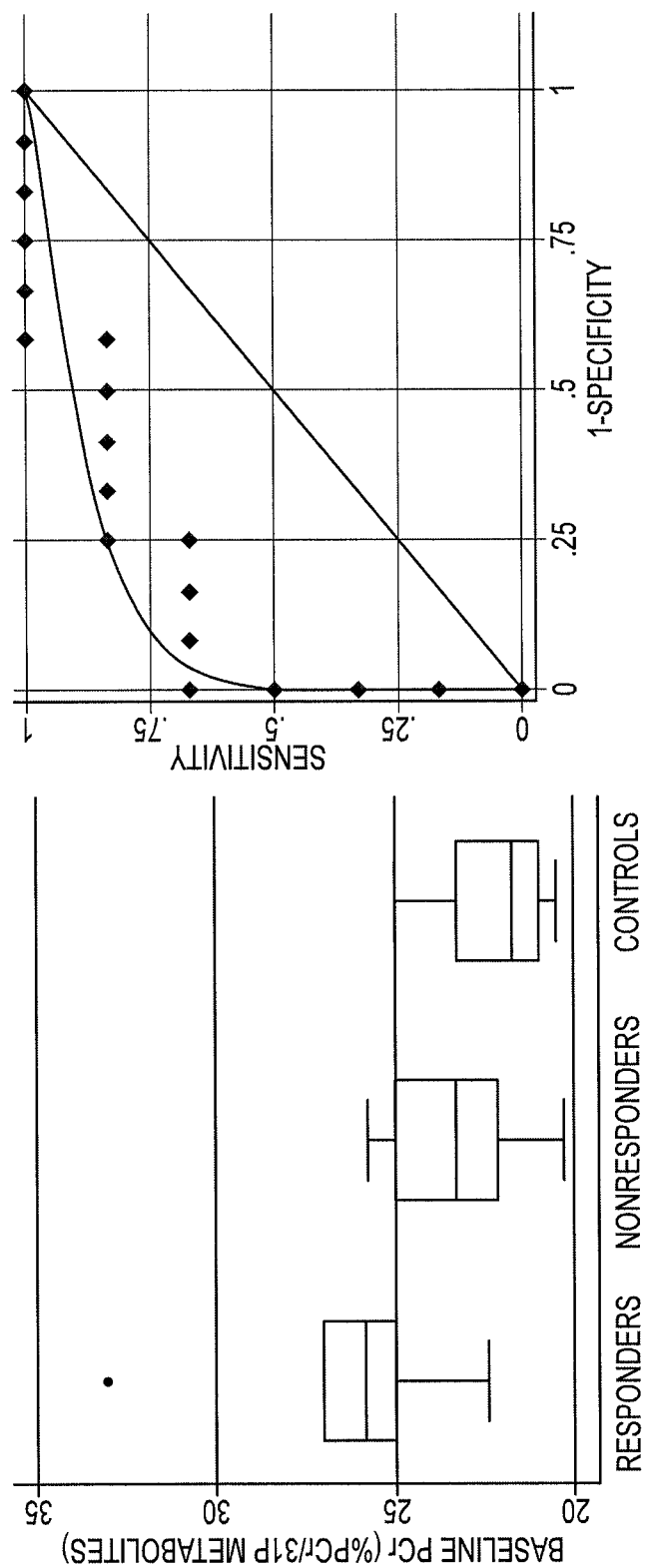

The left panel of FIG. 2 shows baseline phosphocreatine levels, as measured by $^{31}$P magnetic resonance spectroscopy, in normal control subjects and in two groups of subjects having major depressive disorder: one group that manifested reduced symptoms and/or other levels of depression in response to an antidepression treatment, and the other group that did not manifest such reduced levels and/or symptoms of depression in response to an antidepression treatment. The right panel of FIG. 2 indicates the sensitivity and specificity with which baseline brain phosphocreatine levels predict whether a patient suffering from major depressive disorder will manifest reduced levels and/or symptoms of depression in response to an antidepression treatment.

Figure 3:
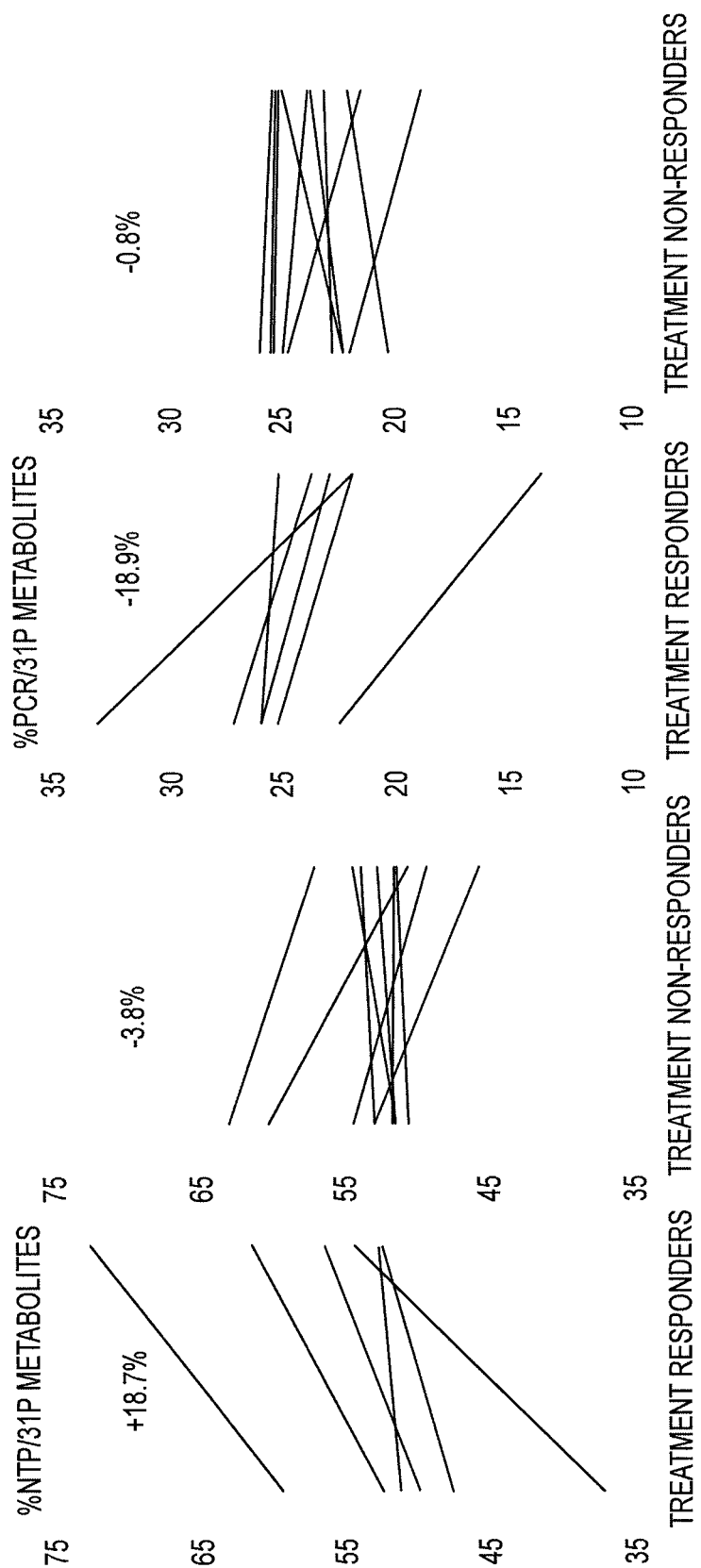

FIG. 3 shows changes in total nucleotide triphosphate levels and in phosphocreatine levels in two groups of major depressive disorder patients: one group that manifested reduced symptoms or other levels of depression in response to an antidepression treatment and the other group that did not manifest such reduced levels or symptoms of depression in response to the antidepression treatment.

DETAILED DESCRIPTION OF THE INVENTIONS

Antidepressant properties of certain hormones can result from their effects on brain bioenergetic metabolism. In theory, certain subjects that suffer from depression and that manifest reduced levels and/or symptoms of depression in response to hormone augmentation could, in response to hormone augmentation, present significant increases in brain bioenergetic metabolism, as indicated by, for instance, brain phosphorous comprising compound levels. In contrast, certain subjects that suffer from depression and that do not manifest reduced levels and/or symptoms of depression in response to hormone augmentation would not, in response to hormone augmentation, present significant increases in brain bioenergetic metabolism.

As used herein, antidepression treatment modalities can include drugs (each drug or combination of drugs representing a different modality); surgery; or electroconvulsive therapy (ECT), for example. Any specific treatment regimen or dose schedule can be considered a different modality.

Some embodiments of the present invention provide methods for determining, in a patient that suffers from depression, a propensity of the patient to manifest reduced levels and/or symptoms of depression in response to an antidepression treatment. Certain embodiments comprise determining, in a brain of a patient that suffers from depression, levels of a marker (e.g., a metabolite) indicative of a brain bioenergetic metabolic state of the patient, the brain bioenergetic metabolic state being predictive as to whether the patient will manifest reduced levels and/or symptoms of depression in response to a depression treatment. In certain embodiments, a level of a marker predictive that the patient will respond to an antidepression treatment modality will normalize in response to the antidepression treatment.

In some embodiments, such a brain bioenergetic metabolic state marker can be, for instance, a pH, a compound comprising magnesium, and a compound comprising phosphorus (e.g., PCr, ATP, ADP, Pi, total NTP, α-NTP, β-NTP, γ-NTP, and combinations thereof). In some embodiments, levels of such phosphorus comprising compounds present in the brain of a patient can be determined by, for instance, $^{31}$P MRS. In certain embodiments, the patient can suffer from MDD. In some embodiments, the patient can suffer from depression resulting from recurring head pain, such as migraine headaches, cluster headaches, and tension headaches. In some embodiments, the antidepression treatment can comprise administering to the patient an SSRI, a tricyclic, a thyroid hormone, or combinations thereof. In certain embodiments, the 17-item Hamilton Rating Scale for Depression (HAMD-17) can be used to determine levels and/or symptoms of depression in the patient.

In certain embodiments, brain levels of ADP, ATP, and PCr are different, as compared to a subject that does not suffer from depression, in the brain of a subject that suffers from depression and that will likely manifest reduced levels and/or symptoms of depression in response to an antidepression treatment. In some embodiments, an antidepression treatment results in a substantial normalization of brain levels of ADP, ATP, and PCr in the brain of a patient that manifests reduced levels and/or symptoms of depression in response to the antidepression treatment. Without being limiting to any particular theory, such normalizing changes in brain PCr and ATP levels in can result in the achievement of a substantially normalized brain bioenergetic metabolic state as a result of the buffer role of PCr in relation to ATP. For instance, brain concentrations of ATP can, at the expense of brain PCr concentrations, normally be maintained at substantially uniform levels by PCr transfer of a high-energy phosphate group to ADP, re-forming ATP in a reaction mediated by, for example, creatine kinase. A reduction of an brain concentration of ADP, ATP, or PCr to a substantially non-physiologic level can result in a brain metabolic state correlated with depression. An antidepression treatment that substantially normalizes a level of ADP, ATP, or PCr in a patient suffering from depression can thereby alleviate a level or symptom of depression in the patient. But such normalizing changes in brain ADP, ATP, and PCr brain concentrations in patients that respond to a depression treatment can also be achieved by other mechanisms.

In certain embodiments, a mitochondrial dysfunction characterizes a patient that manifests reduced levels and/or symptoms of depression in response to an antidepression treatment modality. Without being limited to any particular theory, low levels of magnesium in the brain of a subject that suffers from depression, as compared with normal subjects, can result from impaired oxidative phosphorylation related to mitochondrial dysfunction; and impaired oxidative phosphorylation can result in a brain bioenergetic metabolic state correlated with depression. An antidepression treatment that substantially normalizes, in a patient suffering from depression, brain magnesium levels resulting from mitochondrial dysfunction can alleviate a level or symptom of depression in the patient. But such normalizing changes in levels of magnesium in the brain of a patient that responds to a depression treatment modality can also be achieved by other mechanisms.

$^{31}$P MRS data were acquired from a 20-mm-thick axial slice through the head. We segmented and measured tissue volumes in the proton images acquired with our slice prescription. The total volume of skin, muscle, and bone tissue represents approximately 15% of the acquisition volume. We estimate the muscle tissue alone represents approximately 5% of the acquisition volume, which is consistent with previous studies, which used a similar slice position and found a 5% contribution of muscle to the tissue volume in the slice.

Given that the concentration of ATP and PCr is higher in muscle tissue than in brain, we estimate that 10%-14% of the NTP signal and 15%-30% of the PCr signal recorded in our brain slab might originate in scalp muscle. Thyroid hormones have been shown to increase bioenergetic metabolism in skeletal muscle as well as in the brain. It is therefore possible that thyroid hormones could engender bioenergetic metabolic changes in brain and muscle tissue alike and that such changes (occurring throughout the body) would be related to clinical response to thyroid hormones in depression. In contrast, our interpretation of these data is that changes in $^{31}$P MRS metabolites are related primarily to changes in brain metabolism, changes that occur selectively in treatment responders.

Our results suggest that depressed subjects have abnormal brain bioenergetic metabolism and that the antidepressant effect of thyroid hormone (T3) augmentation of SSRIs is correlated with significant changes in brain bioenergetics, primarily with increases in brain ATP levels and with compensatory decreases in brain PCr. This might be a more general brain mechanism involved in the recovery from depressive episodes. Further studies are needed to determine whether the findings can be generalized to other antidepressant treatments.

Nineteen subjects meeting DSM-IV criteria for MDD who had previously failed to respond to selective serotonin reuptake inhibitor (S SRI) antidepressant drugs received open label and prospective augmentation treatment with T3 for 4 weeks. We obtained $^{31}$P MRS spectra before and after treatment from all MDD subjects and baseline $^{31}$P MRS from nine normal control subjects matched for age and gender. At baseline, depressed subjects had lower intracellular $Mg^{2+}$ compared with control subjects. Seven MDD subjects (38.9%) were treatment responders (≥50% improvement). Total nucleoside triphosphate (NTP), which primarily represents adenosine triphosphate (ATP), increased significantly in MDD subjects responding to T3 augmentation compared with treatment nonresponders. Phosphocreatine, which has a buffer role for ATP, decreased in treatment responders compared with nonresponders.

The antidepressant effect of thyroid hormone (T3) augmentation of SSRIs is correlated with significant changes in the brain bioenergetic metabolism. This seems to be a re-normalization of brain bioenergetics in treatment responders. Further studies will determine whether these findings can be generalized to other antidepressant treatments.

EXAMPLES

Subjects 19 depressed subjects were recruited through advertisements and clinical referrals for a treatment study at Massachusetts General Hospital between 2001 and 2003, and underwent $^{31}$P MRS scans before and after antidepression treatment. All 19 depressed subjects were between ages of 18 and 65, and suffered from MDD, as determined by pre-antidepression treatment score of ≥16 on the HAMD-17 scale. All 19 MDD subjects had previously shown minimal or no response to treatment with an SSRI taken for ≥8 weeks, with ≥4 weeks at a stable dose (fluoxetine ≥40 mg/day, sertraline ≥100 mg/day, paroxetine ≥40 mg/day, citalopram ≥40 mg/day, escitalopram ≥20 mg/day). In addition, nine normal control subjects, matched for age and gender with the 19 MDD subjects, that did not suffer from depression, were not medicated, and had no medical or neurological history of depression underwent $^{31}$P MRS scans matched to the MDD subjects.

After an initial evaluation, all MDD subjects enrolled into a 4-week open treatment with triiodothyronine (T3) 50 μg daily added to their existing SSRI. The HAMD-17 scale was administered every 2 weeks. The MDD subjects had TSH, T3, T4, and free-T4 levels measured before initiation of treatment and at 4-weeks follow-up with a solid-phase radioimmunoassay.

Magnetic Resonance Techniques

All MDD and all control subjects underwent brain $^{31}$P MRS in the 4-T Varian Unity/Inova (Varian, Palo Alto, Calif.) magnetic resonance scanner at the Brain Imaging Center at McLean Hospital. $^{31}$P MRS scans were acquired with a dual tuned, dual quadrature detection, open-face proton-phosphorus TEM whole-head coil (MR Instruments, St. Louis Park, Minn.) operating at nominal frequencies of 170.3 MHz for 1H and 68.9 MHz for $^{31}$P. Two scans for each MDD subject and one scan for each control subject were acquired prior to the treatment period (i.e., baseline) and at the end of the treatment period.

The $^{31}$P MRS scan included subject positioning, frequency, and field homogeneity shimming adjustments over the whole head; acquisition of a series of pilot images; positioning of the slice for $^{31}$P MRS; shimming on the $^{31}$P MRS slice; and acquisition of $^{31}$P MR spectra. The head of each subject was positioned reproducibly relative to the center of the scanner bore and radiofrequency (RF) coil over sessions for each subject with a table laser beam. Pilot proton images were acquired with multi-slice rapid gradient echo proton magnetic resonance imaging in the sagittal, coronal, and axial planes. Sagittal pilot images were used to reproducibly position the 20-mm-thick axial brain slice used for acquisition of the $^{31}$P MRS data from session to session.

Figure 1:
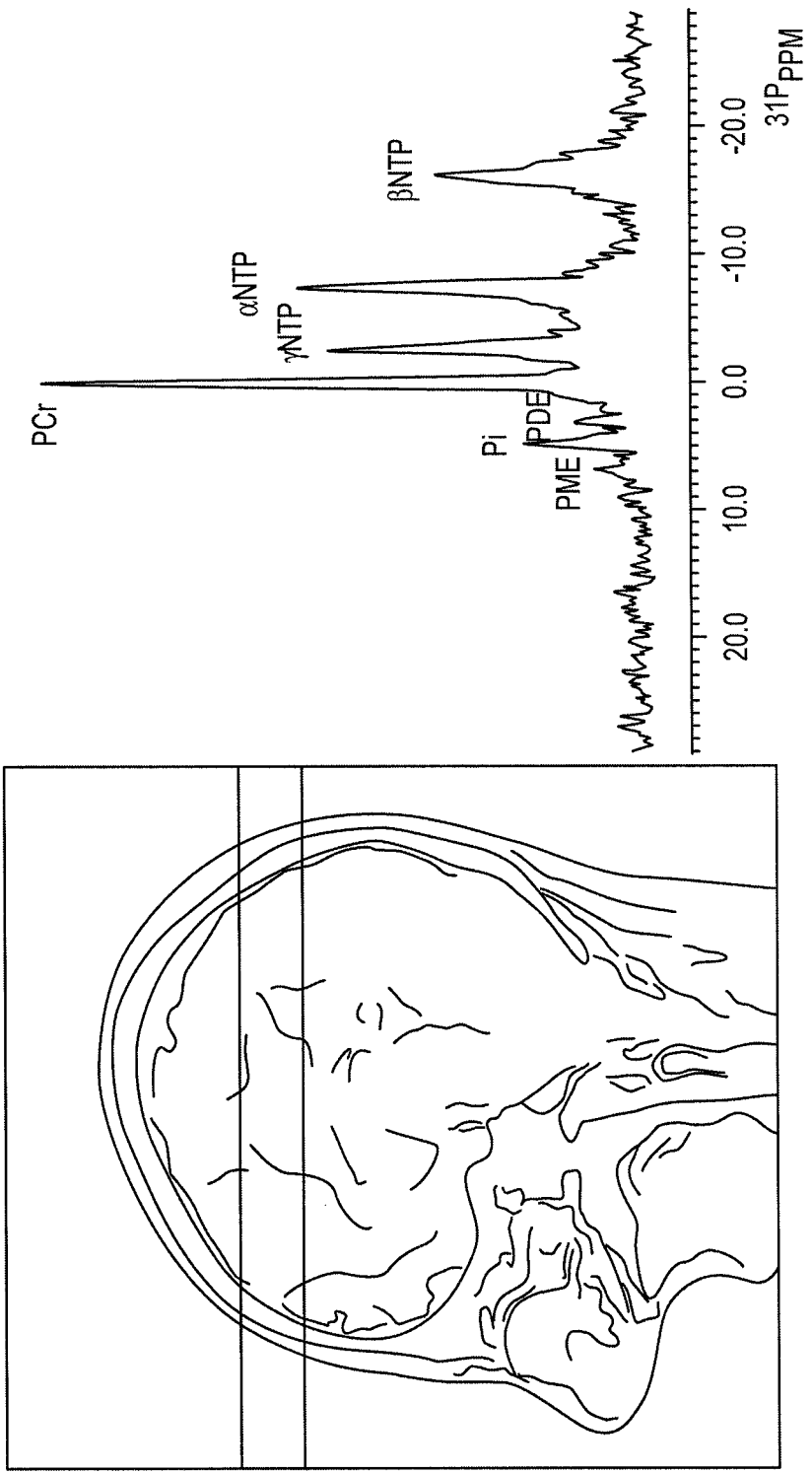
FIG. 1 shows a midsagittal phosphorus magnetic resonance image slice (left panel) a $^{31}$P magnetic resonance spectrum (right panel) of a healthy subject.

Axial proton images of the $^{31}$P MRS brain slice acquired as one 20-mm-thick slice and as five adjacent 4-mm-thick slices were used to determine the contribution of head skin and muscle tissue to the $^{31}$P MRS acquisition volume. The 20-mm-thick axial brain slice was obtained midsagittally through frontal and parietal areas, above the corpus callosum as shown in FIG. 1. The slice was positioned mid-sagittally so as to center the slice in the anterior cingulate cortex. The gradient recalled echo of the $^{31}$P MRS free induction decay signal was acquired from the slice with a standard slice selective sequence. The sequence was implemented by applying a 90° flip-angle 5000 μs-duration frequency-selective 5-lobe sinc-shaped RF pulse simultaneously with a gradient in the slice selection direction, followed by a 2.5-msec phase refocusing gradient and acquisition of the signal.

The following acquisition parameters were applied: number of averaged transients NT=128, number of acquired complex points NP=2048, spectral width SW=4000 Hz, repetition time TR=2000 msec, number of dummy transients DS=4. Application of the refocusing gradient resulted in a delay between RF pulse and acquisition of 2.554 msec. The total scan time was 4 min and 57 sec. The 2-sec repetition time resulted in a substantial attenuation of the phospholipid metabolism peaks (phosphomonoesters (PME) and phosphodiesters (PDE), see FIG. 1) relative to the NTP peaks, owing to differential longitudinal relaxation (T1) saturation effects (at 4T, the PME and PDE T1s are approximately 2.7 and approximately 3.9 sec, respectively, whereas the T1 of ATP is approximately 1.0 sec). This relative signal attenuation due to differential saturation was consistent for all scans.

Statistical Analyses

Spectral resonances were assessed with fully automated, time domain fitting algorithms. Analysis of $^{31}$P MRS in vivo data was performed with a time domain spectral fitting routine based on a nonlinear, Marquardt-Levenburg algorithm in combination with prior spectral knowledge. The individual estimated areas of the peaks from phosphomonoesters (PME), inorganic phosphate (Pi), phosphodiesters (PDE), PCr, and nucleoside triphosphate (γ, α, and β NTP) were normalized by the total phosphorus signal, yielding the percentage of total phosphorus signal intensity contributed by the metabolite peak. The intracellular pH was determined from the chemical shift of Pi relative to PCr. The intracellular concentration of free magnesium ($Mg^{2+}$) was determined from the chemical shift of (-NTP relative to PCr with a semi-empirical equation, taking into account the brain cytosolic pH and the intracellular ionic strength. The researcher performing all metabolite evaluations was blinded to the clinical status of all study subjects.

The reliability of acquired $^{31}$P MRS data was determined by scanning four healthy human volunteers at 4T at two separate times (1 week apart), with the above-described sequence and brain slab positioning. $^{31}$P MRS metabolite values were and the coefficients-of-variance for high-energy phosphate metabolites were determined. For the four subjects the average coefficients of variation between visits were PCr=4% (range=1%-10%), total NTP=2% (range=0.3%-3%), (3 NTP=2% (range=1%-3%), pH=0.07% (range=0.01%-0.23%), $Mg^{2+}$=5.6% (range=0.6%-8.5%).

Differences in demographic and clinical variables between the treatment group and the control group were analyzed with nonparametric tests (Wilcoxon signed rank test for paired data, Wilcoxon rank sum test for unpaired data) and $\chi^2$ tests. Nonparametric Wilcoxon rank sum (Mann-Whitney U) test was used to compare baseline levels of $^{31}$P MRS metabolites between MDD subjects and normal control subjects. Clinical outcome was defined as response to treatment (HAMD-17 reduction ≥50% during treatment). The Wilcoxon rank sum (Mann-Whitney U) test was used to compare changes from baseline to end of study in $^{31}$P MRS metabolites between MDD subjects that manifested reduced levels and/or symptoms of depression in response to the T3 augmentation treatment and those MDD subjects that did not manifest reduced levels and/or symptoms of depression, as determined by the HAMD-17 ranking.

The three main comparisons (1. comparisons of MDD vs. control subjects; 2. comparisons of baseline $^{31}$P MRS metabolites in responders vs. nonresponders; and 3. comparisons of changes in MRS metabolites in responders vs. nonresponders) were each tested at an overall a level of 0.05. Because each of the three comparisons included five metabolites (β-NTP, total NTP, PCr, pH, and $Mg^{2+}$), the p values obtained for individual metabolites were multiplied by 5 to perform Bonferroni corrections of multiple comparisons.

In further analyses, a linear regression was used to assess the relationship between clinical depression improvement (% HAMD-17 change) and changes in $^{31}$P MRS metabolites, controlling for age and gender (together the Bonferroni correction described herein). All analyses were performed with Stata 9.0 for Windows (Stata Corporation, College Station, Tex.). Statistical significance was defined at the p<0.05 level, two-tailed.

Results

The demographic and clinical characteristics of our subjects are presented in Table 1. After 4 weeks of treatment, the mean severity of depression dropped from HAMD-17=20.3±3.6 to HAMD-17=13.3±6.6. Seven subjects (36.8%) were treatment responders (HAMD-17 reduction ≥50%) and six subjects (31.6%) achieved clinical remission (final HAMD-17<7). The results of the open T3 augmentation trial have been reported in detail previously (16). Spectral data on one baseline scan (from a depressed subject, treatment responder) and two post-treatment scans (treatment nonresponders) were of poor quality and could not be used, yielding complete pre- and post-treatment data for 16 subjects (6 treatment responders, 10 nonresponders).

cance after correcting for multiple comparisons [z(14)=−2.435, corrected p=0.064]. Baseline PCr levels predicted treatment response with 79% accuracy (83% sensitivity, 75% specificity) and 0.88 Area Under the Receiver Operating Curve (AUC) (FIG. 2). There were no significant differences in baseline (β NTP, total NTP, pH, and cytosolic $Mg^{2+}$ between responders and nonresponders to T3 augmentation (p>0.05). Compared with depressed subjects not responding to thyroid hormone augmentation treatment, treatment

TABLE 1

Clinical Characteristics of MDD Subjects and Normal Control Subjects

|  | MDD Subjects (n = 19) | Normal Control Subjects (n = 9) | Test Statistic | p |
| --- | --- | --- | --- | --- |
| Age | 43.6 ± 10.0 | 40.0 ± 10.1 | z(26) = −1.05 | .29 |
| Female Gender | 11 (57.9%) | 5 (55.5%) | $x^2(1) = .44$ | .51 |
| SSRI Dose (equivalent mg fluoxetine) | 53.7 ± 29.9 |  |  |  |
| Baseline HAMD-17 score | 20.3 ± 3.6 | .4 ± .7 | z(26) = −4.24 | p < .0001[a] |
| Baseline TSH (mIU/L) | 1.75 ± .71 | 1.97 ± 1.22 | z(26) = .47 | .64 |
| Final TSH (mIU/L) | .10 ± .24 |  |  |  |

MDD, major depressive disorder; SSRI, selective serotonin reuptake inhibitor; HAMD-17, 17-Item Hamilton Rating Scale for Depression (treatment response = HAMD-17 Improvement > 50%); TSH, thyroid-stimulating hormone.
[a] p < .05.

The baseline intracellular free $Mg^{2+}$ was significantly lower in depressed subjects compared with normal control subjects [z(25)=2.78, corrected p=0.03]. There were no significant differences in baseline levels of β NTP, total NTP, PCr, and pH between MDD and control subjects (Table 2).

responders experienced significant increase in total NTP and a compensatory decrease in PCr, which has a buffer role for ATP (Table 3 and FIG. 3). In linear regression analyses the changes in total NTP and PCr during treatment were significantly associated with depression improvement (% change

TABLE 2

Baseline $^{21}$P MRS Metabolite Levels In MDD Subjects and Normal Control Subjects

|  | MDD Subjects (n = 18) | Normal Control Subjects (n = 9) | Test Statistic | p |
| --- | --- | --- | --- | --- |
| Baseline β NTP | 16.13 ± 3.40 | 18.03 ± 2.60 | z(25) = 1.65 | corrected, .50 |
| Baseline Total NTP | 51.85 ± 5.72 | 54.75 ± 5.66 | z(25) = 1.54 | corrected, .60 |
| Baseline PCr | 24.48 ± 2.85 | 22.40 ± 1.76 | z(25) = −2.16 | corrected, .15 |
| Baseline pH | 7.04 ± .03 | 7.02 ± .02 | z(25) = −.51 | corrected, ns |
| Baseline $Mg^{2+}$ (μmol/L) | 152.2 ± 22.7 | 193.8 ± 32.8 | z(25) = −2.78 | corrected, .03[a] |

$^{21}$P MRS, phosphorus magnetic resonance spectroscopy; MDD, major depressive disorder; NTP, nucleoside-triphosphate; PCr, phosphocreatine.
[a] p < .05 after Bonferroni correction for multiple comparisons.

Baseline PCr levels were numerically higher in MDD subjects who responded to T3 augmentation compared with nonresponders, but the difference did not reach statistical signifi- HAMD-17), when adjusting for age and gender (Supplement 1). The associations remained significant when additionally adjusting for intracellular pH and $Mg^{2+}$.

TABLE 3

Change (%) in High-Energy Metabolite Levels During the 4-Week Treatment With T3

|  | Treatment Responders | Treatment Nonresponders | Wilcoxon Rank Sum Test Statistic | p (adjusted for multiple comparisons) | Association With Clinical Improvement (% change HAMD-17) |
| --- | --- | --- | --- | --- | --- |
| βNTP | 4.66 ± 5.40 | −.99 ± 2.10 | z(14) = −2.50 | corrected, .065 | coef = .05 t(3, 12) = 2.40, corrected p = .17 |
| Total NTP | 8.70 ± 5.74 | −2.23 ± 4.42 | z(14) = −3.15 | corrected, .01[a] | coef = .03 t(3, 12) = 3.19, corrected p = .04[a] |
| PCr | −5.07 ± 3.93 | −.24 ± 1.91 | z(14) = 2.71 | corrected, .03[a] | coef = −.70 t(3, 12) = −3.35, corrected p = .03[a] |
| pH | −.01 ± .06 | .02 ± .06 | z(14) = −1.05 | corrected, ns | coef = −1.50 t(3, 12) = −1.03, corrected p = ns |

TABLE 3-continued

Change (%) in High-Energy Metabolite Levels During the 4-Week Treatment With T3

| | Treatment Responders | Treatment Nonresponders | Wilcoxon Rank Sum Test Statistic | p (adjusted for multiple comparisons) | Association With Clinical Improvement (% change HAMD-17) |
|---|---|---|---|---|---|
| $Mg^{2+}$ (μmol/L) | 16.2 ± 22.9 | 20.4 ± 53.1 | z(14) = −.24 | corrected, ns | coef = −.04 t(3, 12) = −1.43, corrected p = ns |

Comparison between responders and nonresponders (nonparametric Wilcoxon rank sum test) and association between changes in metabolite levels and clinical improvement (linear regression, adjusted for age and gender). T3, triiodothyronine; HAMD-17, 17-item Hamilton Rating Scale for Depression; NTP, nucleoside-triphosphate; PCr, phosphocreatine.
$^{a}p < .05$ after Bonferroni correction for multiple comparisons.

A module, as used herein, can refer to its ordinary meaning, and can, in some senses, refers to implementation of program logic. A module may advantageously be configured to execute on one or more processors. A module can include, but is not limited to, software or hardware components such as software object-oriented software components, class components and task components, processes methods, functions, attributes, procedures, subroutines, segments of program code, drivers, firmware, microcode, circuitry, data, databases, data structures, tables, arrays, and variables. A module can also refer to a set of business rules not embodied in a computer program.

A computer or program that performs methods according to embodiments of the inventions can interact with or provide data to a customer's, patient's, or health care worker's computer, including by way of example, any Internet site, private networks, network servers, video delivery systems, audio-visual media providers, television programming providers, telephone switching networks, teller networks, wireless communication centers and the like.

The systems described herein may include, by way of example, processors, program logic, or other substrate configurations representing data and instructions, which operate as described herein. In other embodiments, the processors can comprise controller circuitry, processor circuitry, processors, general purpose single-chip or multi-chip microprocessors, digital signal processors, embedded microprocessors, microcontrollers and the like.

As used herein, "machine-readable medium" and "computer-readable medium" can include, without limitation, software or hardware components such as software object-oriented software components, class components and task components, processes, methods, functions, attributes, procedures, subroutines, segments of program code, drivers, firmware, microcode, circuitry, data, databases, data structures, tables, arrays, variables, magnetic disks, cards, tapes, drums, punched cards, paper tapes, optical disks, barcodes, and magnetic ink characters.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A method for determining, in a patient that has a mood disorder, an expectation of the patient to manifest a reduced severity of the mood disorder in response to a treatment modality, the method comprising:
    determining, in a patient that has a mood disorder, a first baseline level of a metabolic marker in the patient's brain;
    comparing, by a processor, the first baseline level to a second, stored baseline level of the marker, the second baseline level comprising a value or a range of values of the marker in the brain of at least one subject that, while having the mood disorder, was exposed to the treatment modality and was responsive or not responsive to the treatment modality;
    determining, by a processor and based on a difference between the first baseline level and the second baseline level, a classification of the patient as likely to be either a treatment responder or a treatment nonresponder; and
    outputting, by a processor, an indicator of the classification to an output device.

2. The method of claim 1, wherein the mood disorder comprises depression.

3. The method of claim 1, wherein the mood disorder comprises dysthymia.

4. The method of claim 1, wherein the marker comprises adenosine triphosphate, adenosine diphosphate, or phosphocreatine.

5. The method of claim 4, wherein the first and second baseline levels of the marker are determined by $^{31}P$ magnetic resonance spectroscopy.

6. The method of claim 1, wherein the marker comprises magnesium, pH, total nucleoside triphosphate, or β NTP.

7. The method of claim 4, wherein the marker comprises phosphocreatine, and wherein the treatment modality is effective to reduce a level of phosphocreatine in a human subject.

8. The method of claim 6, wherein the treatment modality comprises administering a thyroid hormone to the patient.

9. The method of claim 1, wherein the output device comprises a machine readable medium, a computer memory, a display screen, an LCD, or a paper.

10. The method of claim 1, wherein the mood disorder comprises bipolar disorder.

11. The method of claim 1, wherein the at least one subject was significantly responsive to the treatment modality.

12. The method of claim 1, wherein the marker is detected in a region comprising the anterior cingulate, the amygdala, or the hippocampus of the brain.

13. The method of claim 1, wherein the treatment modality comprises administering a serotonin reuptake inhibitor, a tricyclic antidepressant, an antipsychotic medication, or electroconvulsive therapy.

14. A computer-implemented system for determining, in a patient that has a mood disorder, an expectation of the patient to manifest a reduced severity of the mood disorder in response to a treatment, the system comprising:
  an input module, configured to receive, by a processor, an indicator of a first baseline level of a metabolic marker in the patient's brain;
  a processing module, configured for:
    (a) comparing the first baseline level to a second, stored baseline level of the marker, the second baseline level comprising a value or a range of values of the marker in the brain of at least one subject that, while having the mood disorder, was exposed to the treatment and was responsive or not responsive to the treatment; and
    (b) determining, based on a difference between the first baseline level and the second baseline level, a classification of the patient as likely to be either a treatment responder or a treatment nonresponder; and
  an output module, configured to output, by a processor, an indicator of the classification to an output device.

15. The system of claim 14, wherein the output device comprises a machine readable medium, a computer memory, a display screen, an LCD, or a paper.

16. The system of claim 15, further comprising the output device.

17. The system of claim 14, wherein the mood disorder comprises a depression or bipolar disorder.

18. The system of claim 14, wherein the mood disorder comprises major depression, dysthymia, or a depressive disorder not otherwise specified.

19. The system of claim 14, wherein the system comprises computer software or computer hardware.

20. The system of claim 14, wherein the processing module comprises computer-executable instructions for the comparing and the determining.

* * * * *